United States Patent
Stadeker

(10) Patent No.: US 8,727,771 B2
(45) Date of Patent: May 20, 2014

(54) APPARATUS AND METHODS FOR PROVIDING DENTIFRICE ADVANCEMENT

(75) Inventor: Wilkie J. Stadeker, Marietta, GA (US)

(73) Assignee: Medipurpose Pte Ltd, Singapore (SG)

( * ) Notice: Subject to any disclaimer, the term of this patent is extended or adjusted under 35 U.S.C. 154(b) by 310 days.

(21) Appl. No.: 12/922,986

(22) PCT Filed: Mar. 20, 2009

(86) PCT No.: PCT/US2009/037793
§ 371 (c)(1),
(2), (4) Date: Sep. 16, 2010

(87) PCT Pub. No.: WO2009/117650
PCT Pub. Date: Sep. 24, 2009

(65) Prior Publication Data
US 2011/0045434 A1 Feb. 24, 2011

Related U.S. Application Data

(60) Provisional application No. 61/038,625, filed on Mar. 21, 2008.

(51) Int. Cl.
*A61C 1/10* (2006.01)
(52) U.S. Cl.
USPC ............................................................ 433/82
(58) Field of Classification Search
USPC .......... 433/82, 83, 85, 87, 125, 166; 132/311, 132/401
See application file for complete search history.

(56) References Cited

U.S. PATENT DOCUMENTS

| 1,020,321 | A | * | 3/1912 | Smith ............................. 222/98 |
| 5,692,901 | A | | 12/1997 | Roth et al. |
| 5,871,353 | A | | 2/1999 | Pierce et al. |
| 6,257,886 | B1 | | 7/2001 | Warner |

(Continued)

FOREIGN PATENT DOCUMENTS

| CA | 2718598 | 9/2009 |
| WO | 2009117650 | 9/2009 |

OTHER PUBLICATIONS

International Search Report and Written Opinion dated Jul. 30, 2009 for related PCT Application No. PCT/US2009/037793.

(Continued)

*Primary Examiner* — Sunil K Singh
(74) *Attorney, Agent, or Firm* — Troutman Sanders LLP; Ryan A. Schneider; Benjamin C. Wiles

(57) ABSTRACT

According to various embodiments, a dental prophylaxis angle is provided that includes including a content lumen within the body, wherein the proximal end of the body is attachable to a concentric drive dental handpiece and the distal end of the body includes a denial tip and a content portal proximate the dental tip. The dental prophylaxis angle can also include a collapsible container disposed within the content lumen and in fluid communication with content portal. The dental prophylaxis angle can also include a reciprocating advancement mechanism including a gripping section slidably attached to an exterior surface of the body and at least one member extending through the body and into the content lumen in communication with the proximal end of the collapsible container. When sliding the gripping section proximally along the longitudinal axis of the body the member at least partially compresses the collapsible container in the distal direction.

6 Claims, 5 Drawing Sheets

(56) References Cited

U.S. PATENT DOCUMENTS

| 6,382,971 | B1 | 5/2002 | Randolph | |
|---|---|---|---|---|
| 7,070,412 | B2 | 7/2006 | Stadeker | |
| 2002/0170923 | A1 | 11/2002 | Vatman | |
| 2004/0106083 | A1* | 6/2004 | Pond | 433/125 |
| 2006/0204923 | A1* | 9/2006 | Stadeker | 433/82 |
| 2007/0111159 | A1 | 5/2007 | Stadeker | |

OTHER PUBLICATIONS

Office Action issued by the State Intellectual Property Office of the People's Republic of China dated Aug. 22, 2012 for related Chinese Application No. 200980110238.7.

The Notification of the Second Office Action issued by the State Intellectual Property Office of P.R. China dated Apr. 16, 2013 for related CN Application No. 200980110238.7.

* cited by examiner

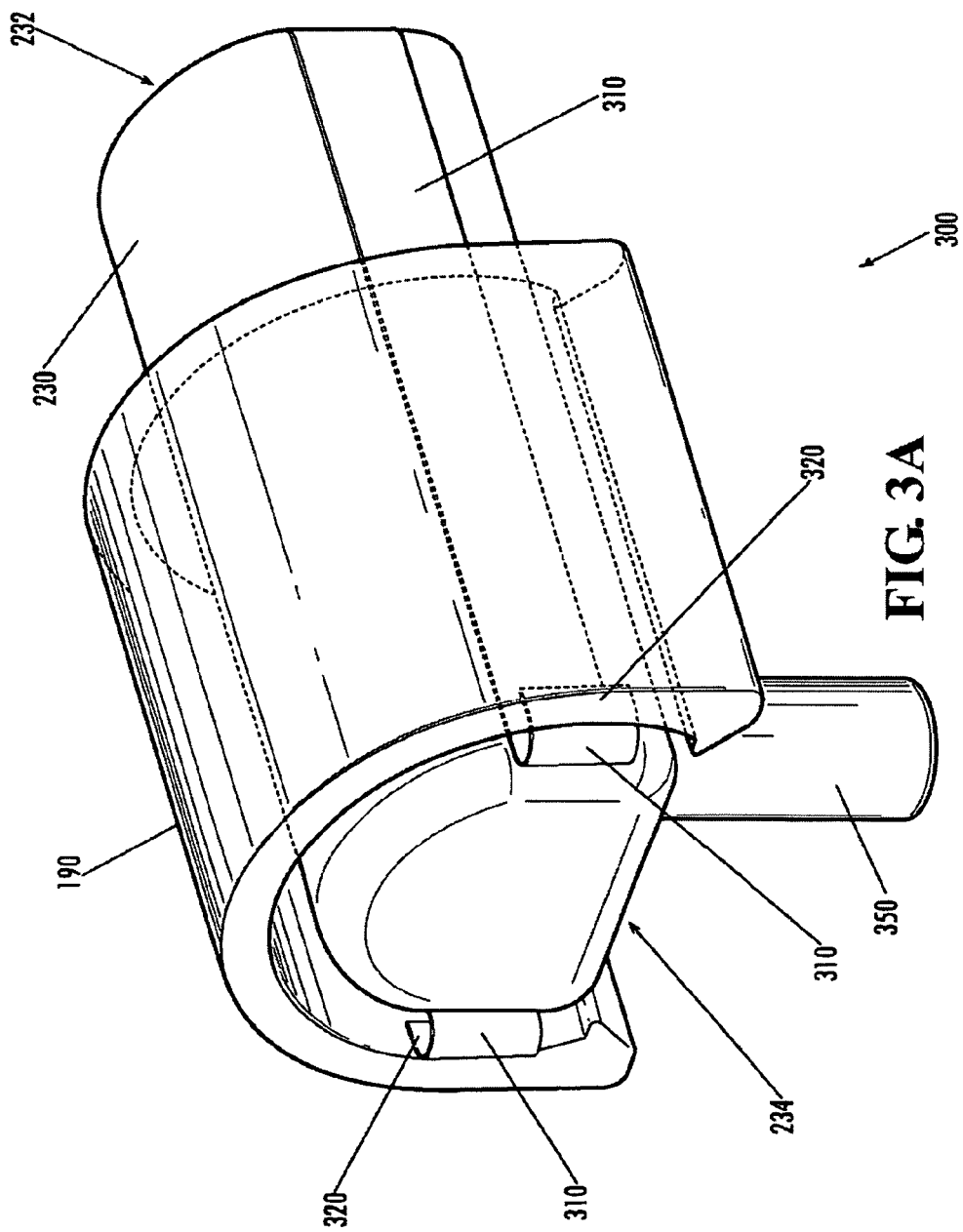

APPARATUS AND METHODS FOR PROVIDING DENTIFRICE ADVANCEMENT

TECHNICAL FIELD

The present invention relates generally to the field of dental devices, and relates more specifically to a self-contained dental prophylaxis angle and therapeutic content advancement mechanism for use in cleaning, polishing, bleaching, bonding, etching, abrading, desensitizing, or otherwise treating teeth.

BACKGROUND OF THE INVENTION

The application of an abrasive dentifrice paste is generally known to clean and polish teeth. Similarly, other dentifrice compounds are applied to the surfaces of teeth in numerous other dental procedures to bleach, abrade, or otherwise treat a variety of dental conditions. Most commonly, such procedures are performed by a dentist, dental hygienist, or dental assistant using a motorized handpiece which receives what is commonly referred to in the art as a "prophylaxis angle" or "prophy angle." Typically, the prophylaxis angle is mounted at a right angle to the handpiece, and has a rotating polishing surface that is rotated by the motorized action of the handpiece, and receives dentifrice as it rotates from a cup mounted on the prophylaxis angle. The dentifrice contained within the cup on the prophylaxis angle is replaced as needed by the operator, typically by dipping the prophylaxis angle into a container of dentifrice and scooping out additional dentifrice as desired.

As conventionally deployed, the dentifrice used in prophylaxis angles has been generally in a paste, cream, or other gummy amalgam form. Powdered dentifrices have also been commonly used, generally with sufficient moisture added to create a paste-like preparation for application.

Formerly, most prophylaxis angles were supplied and used as multi-use devices, requiring cleaning and/or sterilization between use for different patients. With the advent of cost-efficient, disposable manufacturing materials and techniques, and with the growing concern over the prevention of transmittable diseases during dental therapy, the use of single-use, disposable prophylaxis angles has become commonplace.

Although the development of disposable prophylaxis angles has had significant impact on dental practice, problems still exist relating to the application of dentifrice to a patient's teeth using an existing disposable prophylaxis angle. Conventional disposable prophylaxis angles may effectively prevent the spread of disease from patient to patient, but do not completely protect the dentist or other operator from potential exposure during use. The container of dentifrice is often held on the finger of the operator. Digital pressure must then be employed with the dentifrice to apply it to the cup of the prophylaxis angle, and such pressure may often stall the drive motor that drives the prophylaxis angle. As the digital pressure is released, the drive motor overcomes the stalling pressure, and the rotational speed of the prophylaxis cup may suddenly increase, potentially spraying buccal debris such as saliva, blood, and tissue particles into the surrounding work environment. This phenomenon is commonly referred to as "splatter," and may occur even in the presence of a minimal amount of buccal debris. Exposure to such debris can pose a significant health risk to the dentist and/or other operators who are attending the patient.

Past attempts have been made to incorporate dispensable dentifrice within the prophylaxis angle device. However, these efforts have generally failed because of technical disadvantages that prevented their acceptance in the dental marketplace. Among other problems, early prophylaxis angles incorporating paste were not disposable. Additionally, other paste delivery mechanisms were relatively mechanically complex and therefore cost prohibitive.

Furthermore, previously attempted mechanisms for delivering paste contained within a prophylaxis angle are not ergonomically sound and impinge on an operator's ability to control the handpiece. For example, mechanisms on the prophylaxis angle that require pushing a plunger, lever, or knob forward in a direction away from the handpiece may cause loosening of the prophylaxis angle from the handpiece or otherwise interfere with the typical slidable attachment of the prophylaxis angle to the handpiece. Also, mechanisms that require the operator to push a plunger, lever, or knob down in a direction perpendicular to the axis of the prophylaxis angle may interfere with the operator's control and direction of the prophylaxis angle when operating the device, forcing the operator to manipulate the prophylaxis angle counter to the preferred movement during treatment.

For example, disposable prophylaxis angles having internal paste delivery systems using an auger-like structure of the type proposed in the related art must overcome problems associated with charging an internal reservoir with dentifrice material either before or after the auger is assembled into the prophylaxis angle. Either way, the helical blades of the auger, which typically extend for a substantial portion of the internal diameter of the fluid reservoir, make it difficult to fully charge the reservoir with the dentifrice material. Also, the auger blades make advancement of the dentifrice material dependent on the direction of rotation and rotational speed of the auger.

Prophylaxis angles as previously known in the related art are also too large to be practical or were generally more difficult to use and required retraining the practitioner before use on a patient.

Recent efforts to improve a prophylaxis angle are disclosed in U.S. Pat. No. 6,257,886 to Warner, U.S. Pat. No. 6,382,971 to Randolph, U.S. Pat. No. 5,692,901 to Roth et al., and U.S. Pat. No. 5,871,353 to Pierce et al. These cited prophylaxis angles, while they may represent improvements upon certain aspects of the preceding art, continue to be designed around a central rotational axis, which requires more complex engineering to allow for a pathway for dentifrice flow and mechanisms for advancement of the dentifrice. Furthermore, prior methods for manufacturing prophylaxis angles are having more complexly engineered solutions are similarly complex, lacking a simplified, efficient method for alignment and assembly of the constituent components.

The prophylaxis angle disclosed in U.S. Pat. No. 7,070,412 entitled "Self-contained Dental Prophylaxis Angle With Offset Rotation Axis" issued on Jul. 4, 2006 (incorporated by reference in its entirety) provides a dramatic improvement for the delivery of dentifrice material through the angle body with an offset rotational axis, however the mechanism for advancement are not ideally suited.

Accordingly, certain deficiencies also persist among existing prophylaxis angles, leaving a need for further improvement in the design, use, applications, and methods for manufacturing such devices. More specifically, there exists a need for improved mechanisms for advancing therapeutic agents contained within improved prophylaxis angles. There exists a further need for improved design and methods of manufacturing self-contained prophylaxis angles.

SUMMARY OF THE INVENTION

A prophylaxis angle according to the present invention overcomes, or at least alleviates, one or more of the difficulties or deficiencies associated with prior art prophylaxis angles, such as, employing improved mechanisms for advancing dentifrice material through a prophylaxis angle including dentifrice therein, improved prophylaxis angle design for containing dentifrice material therein while also improving ergonomics of the device, and improved methods for manufacturing self-contained prophylaxis angles.

A prophylaxis angle according to one embodiment of the invention includes a dentifrice or other dental therapeutic material dispensed within the prophylaxis angle, and the dentifrice or other dental therapeutic material is dispensed in the proximity of or through the surface tip that cleans or otherwise contacts the teeth for the desired effect.

According to one embodiment invention, a dental prophylaxis angle is provided. The dental prophylaxis angle can include a body having a proximal end a distal end defining a longitudinal axis extending therebetween, and comprising a content lumen within the body, wherein the proximal end of the body is attachable to a concentric drive dental handpiece and the distal end of the body comprises a dental tip and a content portal proximate the dental tip. The dental prophylaxis angle can also include a collapsible container for containing dentifrice, having a proximal end and a distal end and disposed within the content lumen and in fluid communication with content portal. The dental prophylaxis angle can also include a reciprocating advancement mechanism comprising a gripping section slidably attached to an exterior surface of the body and at least one member extending through the body and into the content lumen in communication with the proximal end of the collapsible container. When sliding the gripping section proximally along the longitudinal axis of the body the member at least partially compresses the collapsible container in the distal direction.

According to another embodiment of the invention, a dental prophylaxis angle is provided. The dental prophylaxis angle can include a body having a proximal end a distal end defining a longitudinal axis extending therebetween, and comprising a content lumen within the body, wherein the proximal and of the body is attachable to a concentric drive dental handpiece and the distal end of the body comprises a dental tip and a content portal proximate the dental tip. The dental prophylaxis angle can also include a reciprocating advancement mechanism comprising a gripping section slidably attached to an exterior surface of the body and at least one member extending through the body and into the content lumen. When sliding the gripping section proximally along the longitudinal axis of the body the member is operable to exert a distal force against a removable collapsible container when disposed within the content lumen.

According to one aspect of this embodiment, an end cap can be reattachably connected to the distal end of the body, wherein the collapsible container is insertable into the content lumen through the distal end of the body upon detaching the end cap from the body and exposing the content lumen.

According to yet another embodiment of the invention, a method of manufacturing a dental prophylaxis angle is provided. The method can include providing a body having a proximal end a distal end defining a longitudinal axis extending therebetween, and comprising a content lumen within the body, wherein the proximal end of the body is attachable to a concentric drive dental handpiece and the distal end of the body comprises a dental tip and a content portal proximate the dental tip; and providing a reciprocating advancement mechanism comprising a gripping section and at least one member affixed to and extending between two laterally opposed fixation points on the gripping section. The method can further include positioning the member of the reciprocating advancement mechanism within the content lumen; attaching the gripping section of the reciprocating advancement mechanism to an exterior surface of the body for slidable operation; and positioning a collapsible container having a proximal end and a distal end within the content lumen, the distal end of the collapsible container in communication with the member of the reciprocating advancement mechanism.

According to various aspects of this embodiment, the collapsible container and/or the member of the reciprocating advancement mechanism can be inserted into the content lumen within the body through the distal end of the body.

According to other various aspects of this embodiment, the method of manufacturing a dental prophylaxis handpiece can further include reattachably connecting an end cap over the distal end of the body after positioning the at least one member of the reciprocating advancement mechanism within the content lumen, attaching the gripping section of the reciprocating advancement mechanism to the body, and positioning the collapsible container within the content lumen.

the method of manufacturing a dental prophylaxis handpiece can further include placing a drive mechanism through the distal end of the body and into an offset drive lumen within the body.

According to yet another embodiment of the invention, a dental prophylaxis angle is provided. The dental prophylaxis angle can include a body having a proximal end a distal end defining a longitudinal axis extending therebetween, and comprising a content lumen and an offset drive lumen, wherein the proximal end of the body is attachable to a concentric drive dental handpiece and the distal and of the body comprises a dental tip and an open end exposing a distal end of the content lumen and a distal end of the offset drive lumen. The dental prophylaxis angle can further include an end cap reattachably connected to the distal end of the body to substantially cover the open end. A content container can be insertable into the content lumen through the open end of the body and through the distal end of the content lumen upon detaching the end cap, wherein the content container is positionable in fluid communication with a content portal proximate the dental tip. A drive mechanism can be insertable into the offset drive lumen through the open end of the body and through the distal end of the offset drive lumen upon detaching the end cap, wherein the drive mechanism is operably connectable to the dental tip and a concentric drive dental handpiece.

A dental prophylaxis angle according to various embodiments of the invention may be provided either as a single use, disposable device, or as a reusable device for various applications.

A dental prophylaxis angle according to an embodiment of the invention may be provided for a variety of therapeutic applications in the fields of dentistry and oral hygiene. Such applications include, but are not limited to, the cleaning, polishing, whitening, bleaching, etching, desensitization, bonding, abrading, fluoride treatment of teeth, gums, other intraoral structures, dental appliances, or other dental therapeutic or oral hygienic procedures using the appropriate therapeutic or hygienic material.

A dental prophylaxis angle according to an embodiment of the invention may be provided to mechanically interface with the nozzle connector piece of a standard concentric drive dental handpiece to provide power for use in dental therapeutic or oral hygienic procedures.

In other example embodiments of the invention, a prophylaxis angle may be provided to incorporate a connection allowing direct connection to the motor unit of a standard concentric drive dental handpiece to provide power for use in dental therapeutic or oral hygienic procedures, thus eliminating the need to clean and re-sterilize conventional nozzle connectors for such headpieces.

In yet further example embodiments of the invention, a prophylaxis angle may be dimensioned to decrease the length of the sleeve portion of the prophylaxis angle that interfaces with a standard concentric drive dental handpiece or a nozzle connector piece, allowing for an increased length of the central lumen containing therapeutic material while maintaining substantially the same or smaller overall length of the device relative to previous prophylaxis angles.

A prophylaxis angle according to an embodiment of the invention may be provided as a toothbrush for self use by patients.

A method of treating teeth using a self-contained dental prophylaxis angle according to an embodiment of the invention by an operator or by a patient, in which a dental therapeutic material contained within the dental prophylaxis is delivered to the interface of a powered dental tip and the teeth while power is applied to rotate the dental tip through a drive mechanism which is offset from the mechanical center of the dental prophylaxis unit.

These and other features, aspects, and other advantages of the invention will become better understood with regard to the following drawings and description.

BRIEF DESCRIPTION OF THE DRAWINGS

FIGS. 3A and 3B illustrate partial views of an advancement mechanism of an exemplary self-contained dental prophylaxis angle according to an example embodiment of the invention.

DETAILED DESCRIPTION

Figure 1:
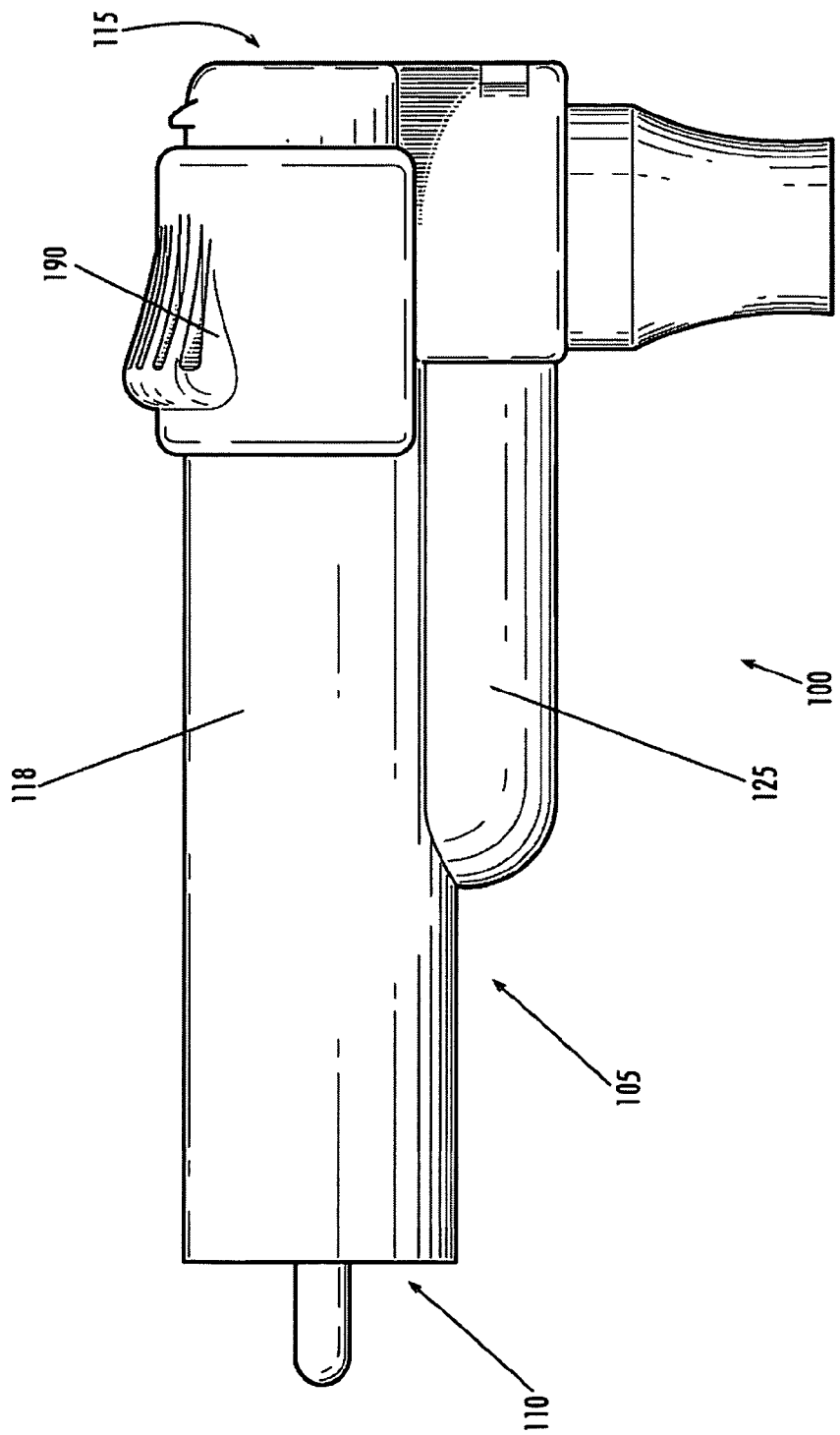
FIG. 1 illustrates an exemplary self-contained dental prophylaxis angle according to an example embodiment of the invention.

Example embodiments of the invention may be understood more readily by reference to the following detailed description and the Examples included herein. However, before the example embodiments of the devices and methods are disclosed and described, it is to be understood that this invention is not limited to the exemplary embodiments described within this disclosure, and the numerous modifications and variations therein that will be apparent to those skilled in the art remain within the scope of the invention disclosed herein. It is also to be understood that the terminology used herein is for the purpose of describing specific example embodiments only and is not intended to be limiting.

Unless otherwise noted, the terms used herein are to be understood according to conventional usage by those of ordinary skill in the relevant art. In addition to the definitions of terms provided below, it is to be understood that as used in the specification, "a" or "an" can mean one or more, depending upon the context in which it is used.

An example embodiment of the invention is directed towards a self-contained dental prophylaxis angle with an offset rotational axis and methods for its use in performing dental therapeutic procedures. Such dental therapeutic procedures, as referred to herein, include, but are not limited to, the cleaning, polishing, etching, desensitization, bonding, abrading, fluoride treatment of teeth, gums, other intraoral structures, dental appliances, or other dental therapeutic or oral hygienic procedures.

In one example embodiment, a self-contained dental prophylaxis angle is provided to dispense dentifrice or other therapeutic medicament contained therein as the prophylaxis angle is being used by an operator to clean or otherwise treat a patient's teeth. An exemplary self-contained dental prophylaxis angle with an offset rotational axis according to the present invention is provided, including an elongated tubular body having a main lumen and optionally an offset drive lumen. A collapsible container operable for containing and dispensing dentifrice or other therapeutic content (referred to interchangeably herein as "dentifrice" and "content") can be disposed within the content lumen of the body. In addition, the offset drive lumen permits an offset rotational drive mechanism to be disposed within the drive lumen, in operable communication with the a standard concentric drive dental handpiece and a dental tip at the distal end of the body. A reciprocating advancement mechanism can be provided to selectively dispense content such as a dental therapeutic dentifrice or other material through the distal content portal into contact or in proximity with the dental tip.

According to one embodiment, the reciprocating advancement mechanism can include a gripping section and a member, such as a rigid or flexible member, affixed to the gripping section and extending through the body into the content lumen. When sliding the gripping section proximally along the longitudinal axis of the body the at least one member at least partially compresses the collapsible container in the distal direction. Accordingly, the gripping section of the reciprocating advancement mechanism can be slidable between a substantially non-compressed position and a substantially compressed position. The substantially compressed position is achieved by sliding the gripping section proximally and causing the member of the reciprocating advancement mechanism to exert a distal force against the proximal end of the collapsible container.

Referring now to the drawings, like numerals indicate like elements throughout the several views. An embodiment of an exemplary prophylaxis angle is shown in FIG. 1. As shown in FIG. 1, an exemplary self-contained dental prophylaxis angle 100 is provided with a tubular body 105 having a proximal end 110 and a distal end 115. Further, the prophylaxis angle 100 may contain at least two parallel lumens, a main lumen 118, and a drive lumen 125. In alternative embodiments, the drive lumen 125 may be encompassed within the main lumen 118. In various embodiments, the external shape of the body 105 may be round, oblong, triangular, square, polygonal, or any other desired shape.

The prophylaxis angle 100 further includes a reciprocal advancement mechanism for delivering therapeutic material, such as dentifrice, contained therein when in use. As illustrated in FIG. 1, an example advancement mechanism includes a gripping member 190 which may be slidably affixed to the body 105 and slide proximally in the body's axial direction when operated to deliver therapeutic content, as is more fully described in reference to FIG. 3.

The prophylaxis angle 100 may be provided either as single use, disposable units, or for multiple use applications. Such prophylaxis angles 100 may be fabricated out of any biocompatible material, including but not limited to, plastics, high durometer rubbers, other polymers, aluminum, stainless steel, other metals, metal alloys, or combinations thereof.

Figure 2:
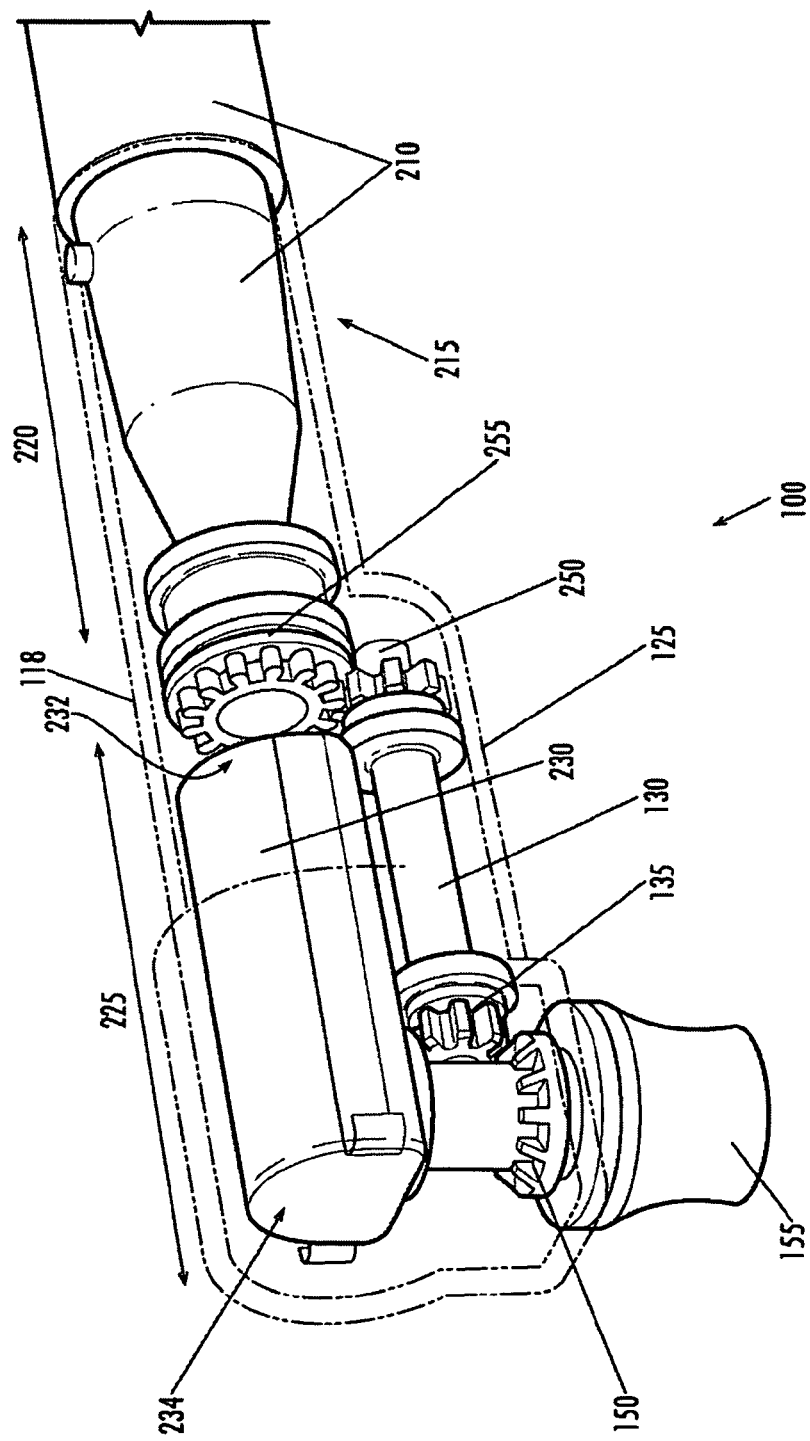
FIG. 2 illustrates a partially transparent view of an exemplary self-contained dental prophylaxis angle according to an example embodiment of the invention.

FIG. 2 provides a semi-transparent illustration of an example self-contained dental prophylaxis angle 100, illustrating example constituent components of the invention, as positioned within the main lumen 118 and the drive lumen 125. The longitudinal axis of the main lumen 118 is referred to herein as the central axis. The drive lumen contains an offset drive shaft 130. The longitudinal axis of the drive shaft 130 is referred to herein as the rotational axis. The drive lumen 125 and thus the rotational axis are offset from the center lumen 118, as is illustrated in FIGS. 1 and 2, so as to make useable space available within the main lumen 118. At the proximal end 110, the offset drive shaft 130 is fitted with a proximal drive gear 250 for connecting to a central drive mechanism 255, including at least a gear in communication with a central drive shaft operably coupled with a standard dental handpiece 210 to provide rotational power to the offset drive shaft 130.

The proximal end 110 of the main lumen 118 may be configured as a sleeve 215 for slidably attaching the prophylaxis angle 100 over the tip of the handpiece 210. In example embodiments of the invention, the sleeve 215 has a sleeve length 220, which may be shorter than previous prophylaxis angles, allowing for a larger reservoir length 225 of the main lumen in which dentifrice or other therapeutic material may be stored. For example, previous sleeve lengths may have measured approximately 21 millimeters or greater, while the sleeve length 220 of the improved prophylaxis angle described herein may measure as little as approximately 13 millimeters and up to approximately 21 millimeters. Thus, reducing the sleeve length 220 to approximately 13 millimeters allows increasing the reservoir length up to approximately 8 millimeters, while keeping the prophylaxis angle 100 substantially the same overall length. Maintaining substantially the same, or reducing, the overall length of the prophylaxis angle 100 will allow for maintaining or improving the ergonomics of the device and thus control, comfort and safety, controlling manufacturing costs, and the like.

The offset drive shaft 130 is further provided with a distal gear tip 135 which interfaces with a geared tip 150 at a distal drive portal to transfer rotational motion from the handpiece to the geared tip 150 thus rotating a dental tip 155 which is attached to the geared tip 150.

It is appreciated that other gear configurations or alternative interfacing means for transferring rotational energy from one member to another may be employed. For example, one or more translational gears may be employed between any of the aforementioned gears.

While the embodiments described above have a separate main lumen 118 and offset drive lumen 125, other embodiments may include a common single lumen accommodates both the drive shaft and content storage/delivery functions.

The dental tip 155 and attached geared tip 150 are rotatably attached to the distal end 115 of the body 105, which may be straight, or may be curved at an angle varying from approximately 0 degrees to approximately 179 degrees with respect to the long axis of the body 105. For example, the dental tips 155 may be square, round, triangular, stellate, heart-shaped, polygonal, or irregular in their various cross-sectional shapes. Such cleaning tips may also be uniform in their long axis dimensions or may be tapered, irregular, or otherwise shaped for optimal use in a given dental therapeutic application. Example dental tips 155 for a prophylaxis angle may be provided with varying durometer material strength, yielding rigid, semi-rigid, or soft dental tips for various applications anticipated by the present invention. For example, the dental tips 155 may be fabricated of plastic, natural or synthetic rubbers, other polymers, nylon, Teflon, plastic foam, metals, metal alloys, ceramics, natural bristles, or other synthetic or natural materials. Such dental tips 155 may further be solid or of varying porosity. In addition, dental tips 155 for a prophylaxis angle according to the present invention may be permanently attached to the prophylaxis angle, or may be removable for use of replacement or alternate form dental tips, as desired by the operator.

At or near the junction with the dental tip 155 and attached geared tip 150, the body 105 may terminate with a content portal that may allow egress of therapeutic content, such as dentifrice, from the main lumen 118 onto or in proximity with the dental tip 155 for cleaning or other therapeutic purposes. In example embodiments of the invention, the therapeutic content may be contained within the main lumen 118 and within a content sac or container 230. The container 230 may be integrated within the main lumen 118 and in fluid communication with the portal of the main lumen 118 such that the therapeutic content therein may only be delivered at or near the dental tip 155 upon compression of the sac 230, otherwise avoiding content leakage. The container 230 may be fabricated of any thin, flexible, and compressible material such as a plastic, rubber, foil, coated paper, or other natural or synthetic polymer. It is preferred that at least the interior surface of the container 230 is chemically inert with respect to the nature of the therapeutic content 230.

The container 230 may further be configured such that its rigidity varies at different portions of the container body. For example, the container 230 may be constructed so as to be more rigid at its proximal portion 232 and less rigid at its distal portion 234, improving the compression characteristics and the ease with which force may be translated from an advancement mechanism applying force to its proximal portion 232. It is further appreciated that in some example embodiments, either the distal portion 234, or both the distal portion 234 and the proximal portion 232, may have increased rigidity, while decreasing the rigidity of the center span of the container between each ends, aiding in the container's ability to compress and eject the content contained therein. The varied rigidity of the container may be accomplished by varying the thickness of the container body, by adding additional materials, such as a substantially rigid end piece, supports, or reinforcements, by constructing the container out of different materials having differing resiliency characteristics, and the like.

It is appreciated that the container 230 may be filled prior to placement within the prophylaxis angle 100, for example, during manufacturing of the container 230. It is further appreciated that the container 230 used may be a container currently being manufactured, having appropriate dimensions for placement within the prophylaxis angle 100 and communication with the portal therein. In one example, the portal may be specifically configured to interface with containers 230 as currently manufactured. However, it is also appreciated that the container 230 may be designed and manufactured specifically for use with the prophylaxis angles 100 as described herein.

Moreover, various embodiments may include multiple therapeutic content containers, such as for dentifrice did for whitening agent.

In other embodiments, a self-contained dental prophylaxis angle 100 may further be provided with a distal cap removable by the operator, which may serve to provide a seal during storage, and to prevent inadvertent leakage of the therapeutic material prior to use. In yet other example embodiments, the distal end may be covered by a membrane. Such a membrane may be solid and removable or pierced by the operator prior to use, or may be semipermeable, and permit egress of the therapeutic material through the membrane when advanced.

A prophylaxis angle according to an embodiment of the invention may further incorporate a control device to start or stop rotational action of the prophylaxis angle for enhanced user control and convenience. Moreover, a prophylaxis angle according to an embodiment of the invention may further incorporate an adjustable geared mechanism to allow user control of the rotational speed of the prophylaxis angle.

FIG. 3A illustrates a partial view of an example prophylaxis angle, including a reciprocating advancement mechanism for delivering therapeutic material from the container positioned within the main lumen of the device, though not illustrating the body of the prophylaxis angle or any other components. More specifically, the reciprocating advancement mechanism 300 includes a digital gripping member 190 and a reciprocating motion imparting flexible member 310 affixed to the gripping member at each fixation point 320 and generally extending to the collapsible container 230 there between forming a reverse directional loop. In one example, the flexible member 310 may be formed as a strap having a substantially flat cross-section. However, it is appreciated that the flexible member 310 may be formed in other cross-sectional shapes, such as having a substantially round cross section and a pocket or larger flat surface at or near the location where it communicates with the container 230.

The flexible member 310 communicates with the container 230 by partially circumscribing the container 230 at or near its proximal portion 232. The flexible member 310 extends from one fixation point 320 on the gripping member 190 through a slot or an orifice in the body of the prophylaxis angle (not shown), which permits freedom of movement therethrough, and into the main lumen. After extending into the main lumen of the prophylaxis angle the flexible member 310 then extends to and around the proximal portion 232 of the container 230, and back through another slot or orifice in the body opposite the previously described orifice, and to the fixation point 320 on the opposite side of the gripping member and external to the body. Accordingly, the two slots or orifices allow for passing the flexible member 310 through the body of the prophylaxis angle and allowing the flexible member to freely slide therethrough, while providing a stationary point of reference relative to the proximally moving gripping member 190 and the distally moving container 230. In one example embodiment, the slots or orifices extend through the body of the device at opposing locations at or near where the distal end 234 of the container 230 would be positioned, allowing for substantial compression of the container 230; though, it is appreciated that in other example embodiments, the location of the slots or orifices may depending upon the configuration of the device, the container 230 within the device, the reciprocal mechanism used, or the like.

Figure 3B:
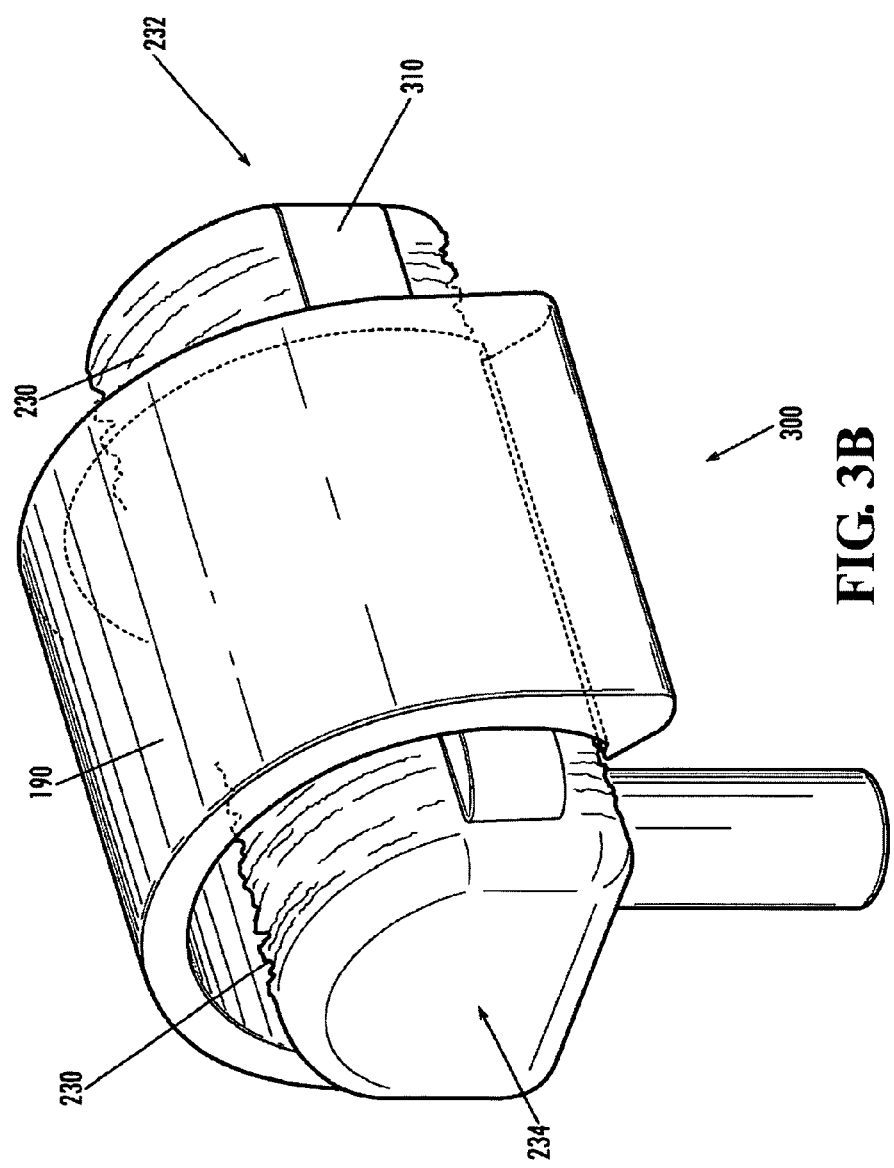

When the advancement mechanism 300 is operated, as illustrated in FIG. 3B, the operator applies a digital force to the gripping member 190 in a direction substantially toward the proximal end of the prophylaxis angle. The force applied to the gripping piece is translated to the flexible member passing through the orifices on either side of the body and in communication with the container. Being passed through the body, which remains at a fixed position relative to the sliding digital gripping member 190, the flexible member 310 thus continues to pass through the orifices and is caused to double back on itself external to the body and in a direction toward the proximal end of the prophylaxis angle. As the gripping member 190 is pulled toward the proximal end of the prophylaxis angle, the flexible member follows external to the body, shortens within the body, and thus reciprocally transfers force to the proximal end 232 of the container 230, compressing it toward its distal end 234. Accordingly, the operator may simply control the delivery of therapeutic material existing within the container 230 by controlling the distance the gripping member is proximally pulled.

Pulling the gripping member 190 proximally toward the handpiece is advantageous because it further exerts a force on the prophylaxis angle against tip of the handpiece, further seating the sleeve on the handpiece. Additionally, the advancement mechanism described herein is simple in design, contains few moving parts, and thus promotes simple, reliable operation and efficient manufacture.

It is appreciated that other example embodiments of the gripping member may be employed. For example, the gripping member may include protrusions or a high friction surface to aid in gripping during use. The gripping member may also include a knob, inverse trigger, loop, or other extending member for increased communication with and control over by the operator. The gripping member and the body of the prophylaxis angle may be configured to include a one-way ratcheting mechanism to prevent the member from sliding distally after being pulled proximally during use. The ratcheting mechanism may be spaced apart and/or associated with graduations providing for further control over the precise volumes of dentifrice being delivered. An embodiment employing a ratcheting mechanism may further include a release, allowing the operator to reposition the gripping member and loosen the tension on the container. Similar to a ratcheting mechanism, the gripping member may include a biased pin or other engagement member and the body of the prophylaxis angle may include a series of receivers, allowing the operator to selectably restrain movement of the gripping member by engaging the pin or other member at a chosen location. It is appreciated that other means for selectably moving and/or restraining the gripping member may be employed with the prophylaxis angle described herein.

In other example embodiments of the invention, the orifices in the body of the prophylaxis angle through which the flexible member extends can permit only transverse motion in one direction, such as a cleat or valve, to prevent loss of pressure against the container. In alternative embodiments, the reciprocal pivoting force can be provided by slots or posts mounted on the distal end of the container, rather than slots in the prophylaxis angle body. Such fixed points can allow the flexible member to move bi-directionally or only in one direction.

It is further appreciated that in other example embodiments, the reciprocal advancement mechanism may not include a flexible member as previously described, but include other means for imparting a reciprocal force when acted on. For example, in one embodiment the gripping member 190 may include at least one lever extending from a gripping member and in communication with a container within the prophylaxis angle. The lever may have a fixed fulcrum such that when the gripping member is pulled proximally along the axis of the main lumen, the lever rotates about its fulcrum and imparts a reciprocal force distally along the axis to the container, causing it to collapse. Other means for imparting reciprocal motion and force by the gripping member to the container may be employed.

In other example embodiments of the invention, the body of the prophylaxis angle may further be provided with one or more transparent windows that permit an operator to monitor the movement or compression of the container towards the distal end of the device, thus allowing the operator to determine how much therapeutic material remains to be dispensed. Additionally, graduations or other markers may be provided on the windows to allow the operator to quantitate the remaining material.

Figure 4:
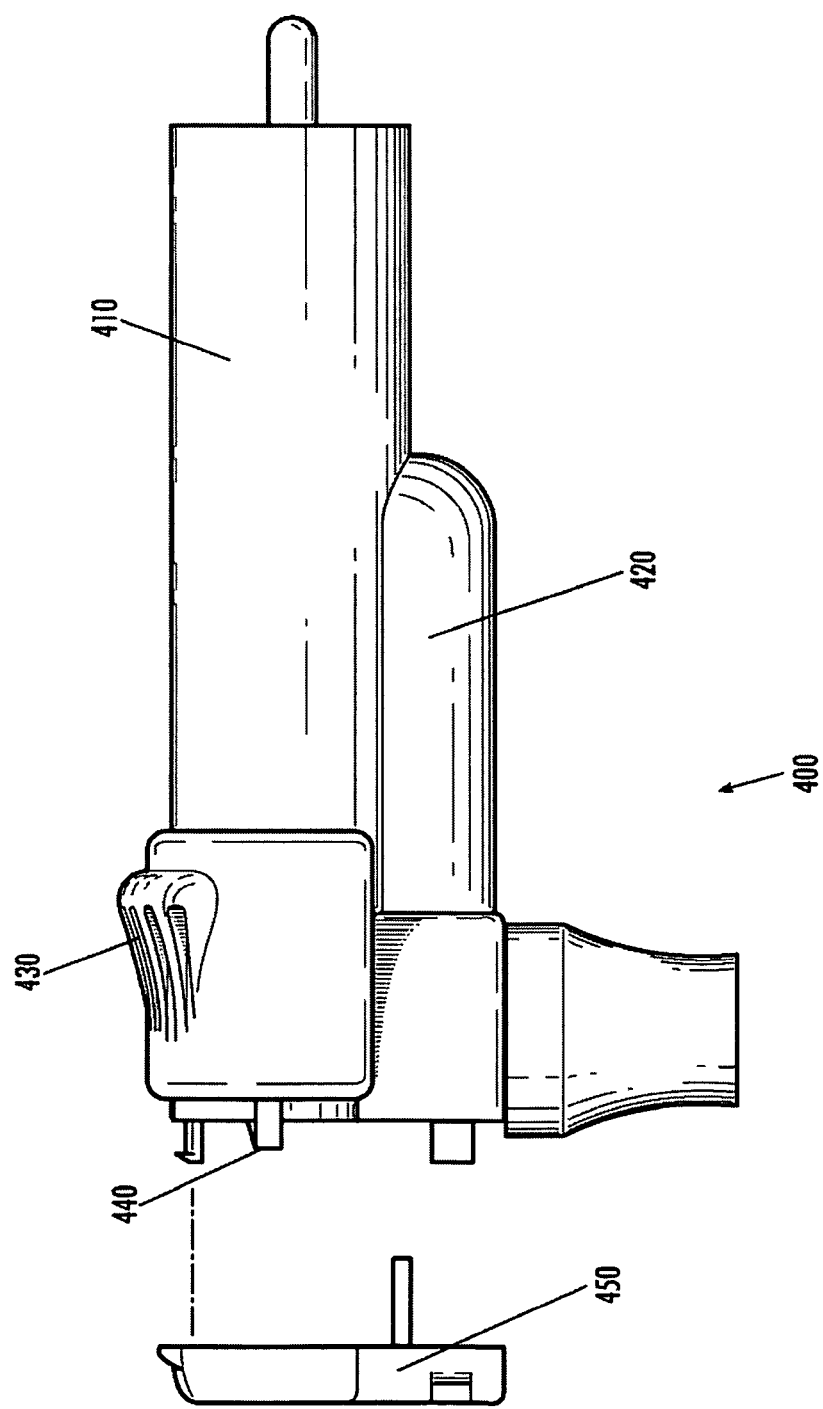
FIG. 4 illustrates an exemplary self-contained dental prophylaxis angle according to an example embodiment of the invention.

FIG. 4 illustrates another example embodiment of a prophylaxis angle in accordance with the invention. The prophylaxis angle 400 includes a main lumen 410, an offset drive lumen 420, and an advancement mechanism including a gripping member 430 and flexible member 440, all described more fully with reference to FIGS. 1-3. The prophylaxis angle 400 includes an end cap 450 which may be removably connected to the distal end of the prophylaxis angle 400. The end cap 450 may be connected to the body of the device by means which are known, including retainer clips, adhesive, screws, pins, and the like. The end cap 450 when removed exposes the distal ends of both the main lumen 410 and the offset drive lumen 420.

Accordingly, the removable end cap 450 may be advantageously used during manufacturing to assemble the constituent components of the device. For example, once the end cap 450 removed (or before being affixed) a container including therapeutic material, such as dentifrice, as described more fully in reference to FIGS. 2 and 3, may be inserted through the distal end of the main lumen 410. In addition to the insertion of the container, or in conjunction therewith, a mechanical advancement mechanism may be inserted through the distal end of the main lumen 410. Further, an offset drive mechanism, as described more fully in reference to FIG. 2 may be inserted through the offset drive lumen 420. In some configurations, it is appreciated that a geared dental tip may be inserted through the distal end of the offset drive lumen 420. Additionally, in some configurations, a central drive mechanism, as described more fully in reference to FIG. 2, may be inserted through the distal end of the main lumen 410. For example, when inserting the central drive mechanism through the distal end of the main lumen 410, the central drive mechanism may be installed, then the container and optionally the advancement mechanism. Though, it is appreciated that some of the aforementioned components may be alternatively be installed through the an open proximal end of the main lumen.

After inserting the constituent component parts through the distal end of device, the end cap 450 may then be affixed to the device, substantially sealing and/or containing the components within the prophylaxis angle 400. In some example embodiments, the end cap 450 may facilitate aligning and securing components installed within the device in place. For example, the end cap 450 may include on its interior surface additional protrusions, tabs, retainer clips, and the like for interfacing, exerting pressure, and/or maintaining the placement of certain components installed within the lumens.

Additionally, in an embodiment employing an advancement mechanism as described with reference to FIGS. 3A and 3B, the orifice through which the flexible member passes may be created by the interface of the end cap 450 with the body of the prophylaxis angle 400. In one example, a notch may be formed in the end cap 450 at a point where the end cap 450 communicates with the main lumen 410 of the device; thus, when attached the notched area not communicating with the main lumen will define the orifice. In another example, the notch may be formed in the interfacing surface of the main lumen 410, and the end cap 450 may be substantially flat. It is also appreciated that the orifice may be formed separately within the body of the prophylaxis angle, and that the end cap 450 and the main lumen 410 create a substantially flush interface.

Accordingly, when assembling a prophylaxis angle 400 including the advancement mechanism previously described and a removable end cap 450, the gripping member 430 is slidably affixed to the body of the device, with the flexible member 420 extending through the distal end and into the main lumen 410. Next, the container would be inserted into the main lumen 410 and positioned to communicate with the flexible member as described above. The additional drive components and/or tip may then be installed through the distal end of the offset drive lumen 420. After all of the components are installed, optionally including the installation of other components as previously described, the end cap 450 may then be affixed to the body of the prophylaxis angle, maintaining the alignment of the flexible member 430 through the orifice so formed.

In use by an operator, an exemplary prophylaxis angle, such as those described above with reference to FIGS. 1-4, is attached to a standard dental handpiece. The rotary motion of the handpiece powers the motion of the central drive shaft, which is transferred to the offset drive shaft, which then in turn is transferred to and causes rotational motion of the dental tip. When the operator desires to effect the dispensing of therapeutic content contained within the device, digital force in the proximal direction on the gripping member transfers the force to the flexible member and then to the container, causing the container to collapse in approximate proportion to the force applied and/or the distance that the gripping member travels relative to the body of the prophylaxis angle. The collapsing of the container causes the therapeutic content to dispense through the port at or near the dental tip.

An alternative embodiment of the invention may include a self-contained dental prophylaxis device similar to the one described above and in reference to FIGS. 1-4, with the further attachment or integration of a motor segment including a tubular or solid motor housing, a commonly available compressed gas-driven motor of conventional design for use in standard dental handpieces, and one or more gas supply connectors sized and located to permit attachment of the entire motor segment, nozzle segment, and prophylaxis angle to a conventional dental handpiece supply line. When a dental prophylaxis angle is provided with an integral or attached motor unit, a motor speed control valve may further be provided with an attached motor speed control device which may be a lever pivotably mounted to a pivot mount, such that pressure on the lever may open the flow of compressed gas through the control valve, allowing the motor to turn with increased speed. The action of this lever may be spring-loaded or otherwise controlled mechanically, such that release of pressure on the lever by an operator causes the motor to slow or stop. Alternately, other mechanical, electrical, or electromechanical speed control connections may be provided between the control lever or alternate control interface and the control valve, providing other conventional mechanisms to decrease or increase motor speed by adjusting the flow of compressed gas to the motor. The action of the speed control device thus allows an operator to regulate the flow of compressed gas to the motor to control its operation and operating speed.

The dentifrice or therapeutic content contained within a prophylaxis angle may be a cleaning paste, a bleaching or etching agent, an antibacterial agent, topical fluoride or calcium treatment, desensitizing treatment, or any other desired therapeutic material or any combination thereof that may be prepared, contained, and delivered in a paste, gel, or other semisolid form. A dentifrice or therapeutic content may also include a surfactant or other chemical, biological, or mechanical agent to aid in the performance of a variety of dental therapeutic procedures.

Location of the drive mechanism needed to power motion of the dental tip in a position that is offset from the longitudinal axis of the body is important to the proper function of a dental prophylaxis angle according to example embodiments of the invention. This offset location permits a mechanical and operational separation in the functions of providing power to the rotating dental tip and of dispensing dentifrice or other therapeutic content.

In yet another alternate embodiment of the invention, a prophylaxis angle may be provided with an offset drive mechanism and a dispensing system for contained dentifrice or other therapeutic medicaments in the form of a motorized toothbrush or other personal dental therapeutic device, designed for use by an operator and/or self use by a patient. In such an application, the prophylaxis angle has either a removable connection from a separate motorized handpiece to provide power, or such a motorized handpiece may be integrated into the prophylaxis angle to provide power and an operating handle.

Finally, while there have been shown and described and pointed out fundamental novel features of example embodiments of the invention, it will be understood that various omissions and substitutions and changes in the form and details of the devices illustrated, and in their operation, and in the method illustrated and described, may be made by those skilled in the art without departing from the spirit of the invention as broadly disclosed herein.

The claimed invention is:

1. A dental prophylaxis angle, comprising:
   a. a body having a proximal end a distal end defining a longitudinal axis extending therebetween, and comprising a content lumen within the body, wherein the proximal end of the body is attachable to a concentric drive dental handpiece and the distal end of the body comprises a dental tip and a content portal proximate the dental tip;
   b. a collapsible container for containing dentifrice, having a proximal end and a distal end and disposed within the content lumen and in fluid communication with content portal; and
   c. a reciprocating advancement mechanism comprising a gripping section slidably attached to an exterior surface of the body, and at least one member extending through the body and into the content lumen , the at least one member comprising at least one flexible member partially circumscribing the collapsible container at the proximal end of the collapsible container, wherein when sliding the gripping section proximally along the longitudinal axis of the body the at least one member at least partially compresses the collapsible container in the distal direction;
   wherein the gripping section of the reciprocating advancement mechanism comprises a first fixation point and a second fixation point laterally opposing the first fixation point, wherein the body comprises a first orifice and a second orifice laterally opposing the first orifice, wherein a first end of the flexible member is affixed to the first fixation point and a second end of the flexible member is affixed to the second fixation point and the flexible member extends through the first orifice and the second orifice into the content lumen, and wherein the first fixation point and the second fixation point are positioned to selectively align with the first orifice and the second orifice, respectively.

2. The dental prophylaxis angle of claim 1, wherein the gripping section of the reciprocating advancement mechanism is slidable between a substantially non-compressed position and a substantially compressed position, wherein the substantially compressed position is achieved by sliding the gripping section proximally and causing the at least one member of the reciprocating advancement mechanism to exert a distal force against the proximal end of the collapsible container.

3. The dental prophylaxis angle of claim 1, wherein the at least one member is operable to slide through the first orifice and the second orifice and in the proximal direction external to the body and to shorten in the distal direction within the content lumen, at least partially compressing the collapsible container in the distal direction, when sliding the gripping section of the reciprocating advancement mechanism proximally along the longitudinal axis of the body.

4. The dental prophylaxis angle of claim 1, wherein the collapsible container is removable.

5. A dental prophylaxis angle, comprising:
   a. a body having a proximal end a distal end defining a longitudinal axis extending therebetween, and comprising a content lumen within the body, wherein the proximal end of the body is attachable to a concentric drive dental handpiece and the distal end of the body comprises a dental tip and a content portal proximate the dental tip; and
   b. a reciprocating advancement mechanism comprising a gripping section slidably attached to an exterior surface of the body, and at least one member extending through the body and into the content lumen, wherein when sliding the gripping section proximally along the longitudinal axis of the body the at least one member is operable to exert a distal force against a removable collapsible container when disposed within the content lumen;
   the at least one member comprises at least one flexible member for partially circumscribing the removable collapsible container at the proximal end of the removable collapsible container, wherein the gripping section of the reciprocating advancement mechanism comprises a first fixation point and a second fixation point laterally opposing the first fixation point, wherein the body comprises a first orifice and a second orifice laterally opposing the first orifice, wherein a first end of the flexible member is affixed to the first fixation point and a second end of the flexible member is affixed to the second fixation point and the flexible member extends through the first orifice and the second orifice into the content lumen, and wherein the first fixation point and the second fixation point are positioned to selectively align with the first orifice and the second orifice, respectively.

6. The dental prophylaxis angle of claim 5, further comprising a removable collapsible container for containing dentifrice, having a proximal end and a distal end and disposed within the content lumen in fluid communication with the content portal, wherein the at least one member of the reciprocating advancement mechanism is in communication with the proximal end of the collapsible container.

* * * * *